(12) United States Patent
Erdlen et al.

(10) Patent No.: US 8,357,330 B1
(45) Date of Patent: Jan. 22, 2013

(54) ANTI-MICROBIAL CATHETER SYSTEM

(76) Inventors: Kelly Erdlen, Dunedin, FL (US); Susan Wren-Carpenter, Seminole, FL (US)

( * ) Notice: Subject to any disclaimer, the term of this patent is extended or adjusted under 35 U.S.C. 154(b) by 0 days.

(21) Appl. No.: 13/199,160

(22) Filed: Aug. 22, 2011

(51) Int. Cl.
*A61L 2/10* (2006.01)
*A61L 2/00* (2006.01)

(52) U.S. Cl. .......... 422/24; 422/22; 422/23; 250/455.11

(58) Field of Classification Search ............ 250/455.11; 422/24, 23, 22; 604/256
See application file for complete search history.

(56) References Cited

U.S. PATENT DOCUMENTS

| | | | | |
|---|---|---|---|---|
| 5,166,528 | A * | 11/1992 | Le Vay | 250/455.11 |
| 6,274,100 | B1 * | 8/2001 | Shepherd et al. | 422/186.3 |
| 6,433,343 | B1 * | 8/2002 | Cimino et al. | 250/455.11 |
| 6,811,748 | B2 * | 11/2004 | Ettlinger et al. | 422/24 |
| 7,175,806 | B2 * | 2/2007 | Deal et al. | 422/24 |
| 7,485,258 | B2 * | 2/2009 | Burger et al. | 422/22 |
| 7,829,016 | B2 * | 11/2010 | Deal et al. | 422/24 |
| 7,922,701 | B2 * | 4/2011 | Buchman | 604/256 |
| 2002/0162972 | A1 * | 11/2002 | Pleet | 250/492.1 |
| 2002/0168287 | A1 * | 11/2002 | Eckhardt et al. | 422/24 |
| 2006/0228251 | A1 * | 10/2006 | Schneberger et al. | 422/23 |

* cited by examiner

*Primary Examiner* — Nikita Wells
*Assistant Examiner* — Johnnie L Smith

(57) ABSTRACT

An exterior container has a primary base, side walls and an open top. A primary floor is located in the exterior chamber and forms an operational chamber. An interior container has a square secondary floor, side walls and top. The interior container is removably received within the exterior container. A retainer is positioned within the interior chamber for receiving a catheter. A source of light is provided within the exterior chamber to irradiate the catheter.

4 Claims, 2 Drawing Sheets

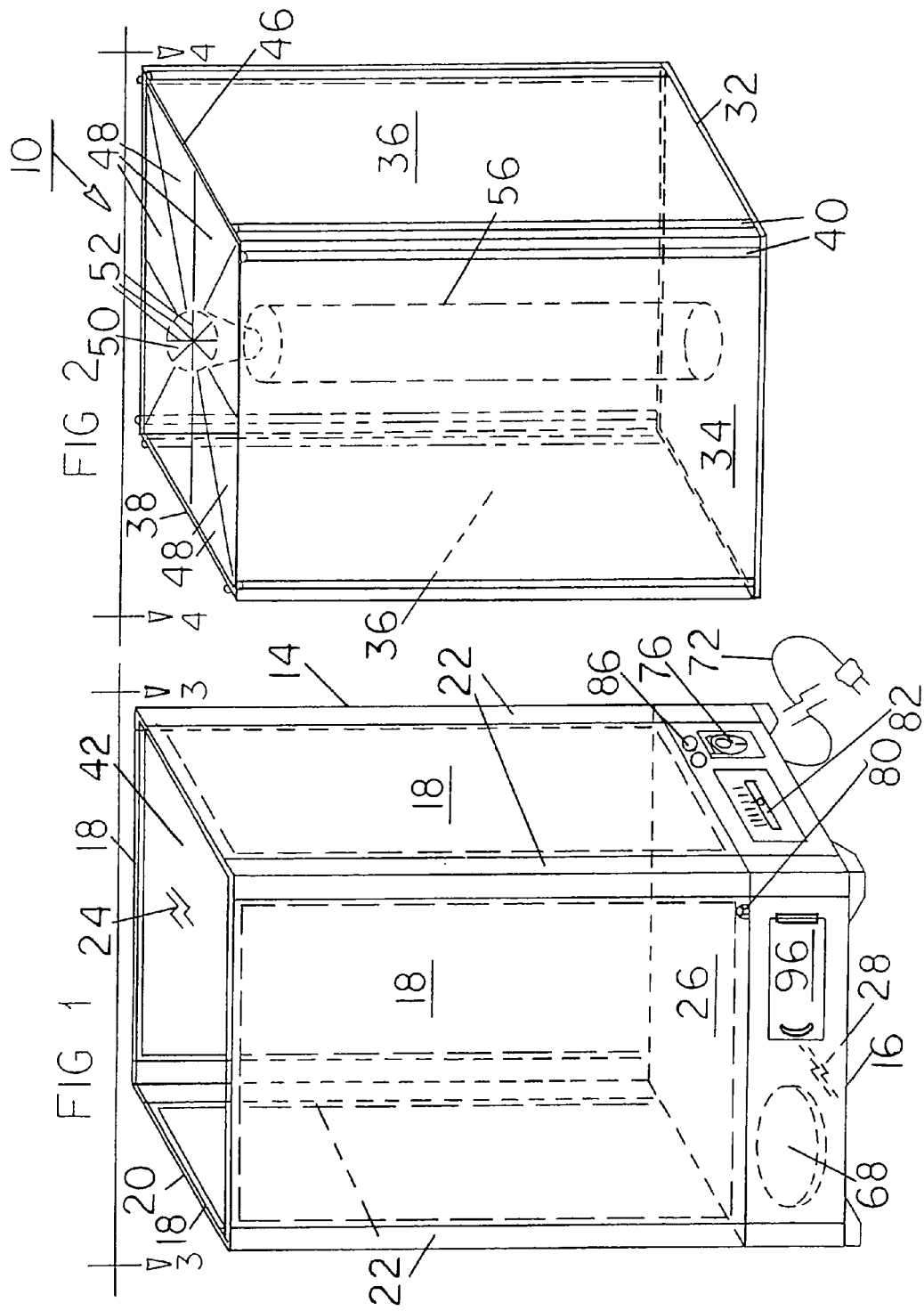

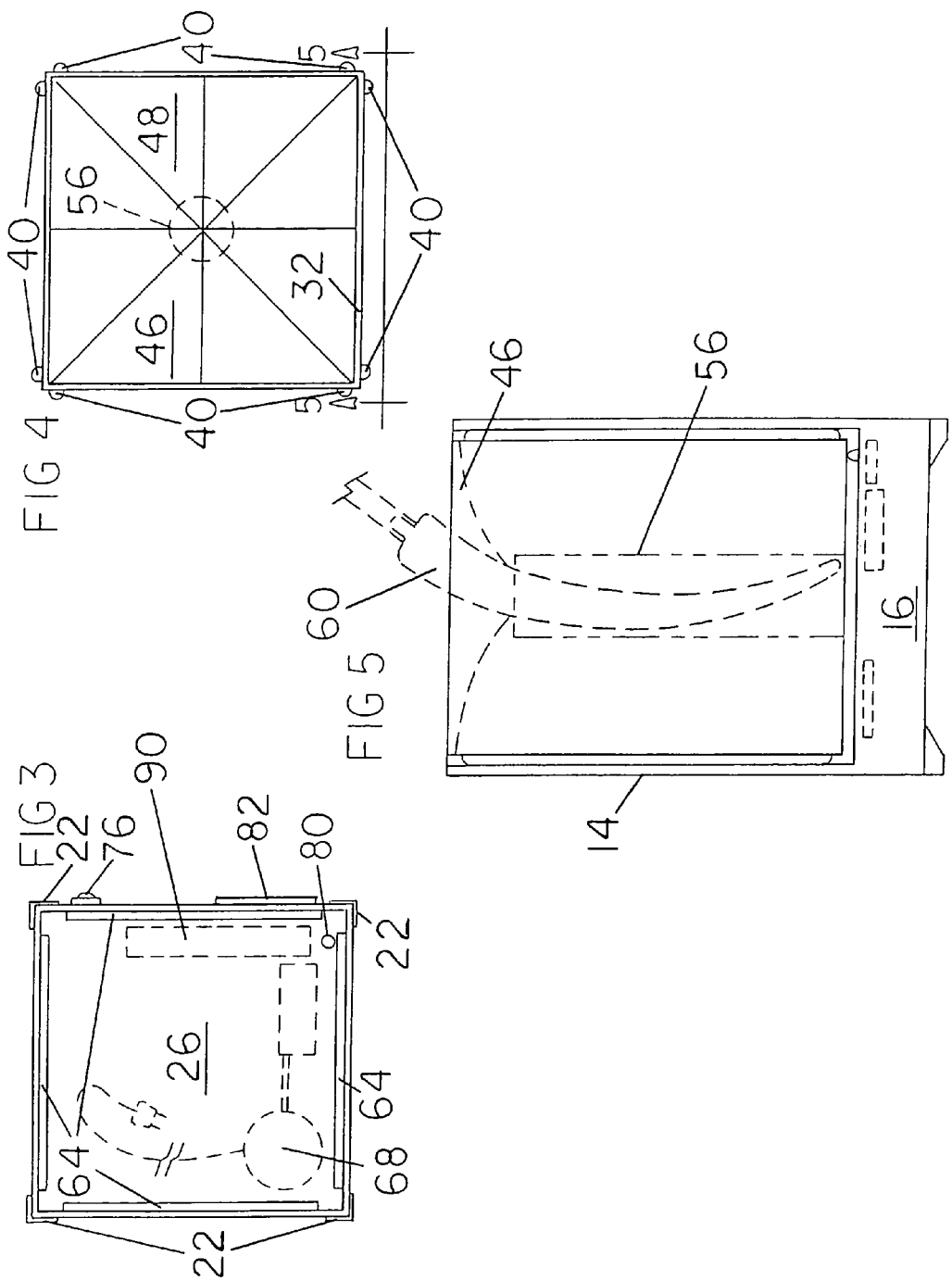

ANTI-MICROBIAL CATHETER SYSTEM

BACKGROUND OF THE INVENTION

Field of the Invention

The present invention relates to an anti-microbial catheter system and more particularly pertains to receiving and supporting and sanitizing an oral-pharyngeal suction catheter, the receiving and supporting and sanitizing being done in a safe, sanitary, convenient and economical manner.

SUMMARY OF THE INVENTION

In view of the foregoing disadvantages inherent in the known types of catheter systems of known designs and configurations now present in the prior art, the present invention provides an improved anti-microbial catheter system. As such, the general purpose of the present invention, which will be described subsequently in greater detail, is to provide a new and improved anti-microbial catheter system and method which has all the advantages of the prior art and none of the disadvantages.

To attain this, the present invention essentially comprises an anti-microbial catheter system. First provided is an exterior container. The exterior container is in a rectilinear configuration. The exterior container has a square primary base. The exterior container has a plurality of similarly configured rectangular primary side walls. The exterior container has an open primary top. The exterior container has vertical primary supports. In this manner the primary side walls are secured together along abutting edges of adjacent primary side walls. The primary base and side walls form a rectilinear exterior chamber. The exterior container has a square primary floor. The primary floor is located in the exterior chamber in proximity to and above the base. An operational chamber is provided. The operational chamber is located between the base and the primary floor. The exterior chamber has a height and a width. The primary side walls are fabricated of an opaque material.

An interior container is provided. The interior container is in a rectilinear configuration. The interior container has a square secondary floor. The interior container has a number of UVC light sources similarly configured rectangular secondary side walls. The interior container has a secondary top. The interior container has vertical secondary spacers along abutting edges of adjacent secondary side walls. The secondary base and side walls form a rectilinear interior chamber. The interior chamber has a height and a width. The interior container is removably received within the disposable exterior container. The secondary side walls are fabricated of a transparent material.

A cover is provided. The cover is fixedly positioned in the interior container. The cover has rigid segments. The cover has an elastomeric center. The center has slits. The slits are provided in a cross/X/or star shaped pattern. The segments have an exterior periphery. The periphery is attached to the interior secondary side walls.

A cylindrical retainer is provided. The cylindrical retainer has an upper edge. The upper edge is located adjacent to the cover. The cylindrical retainer has a lower edge. The lower edge is attached to the secondary floor. The retainer has a diameter. The diameter of the retainer is between 25 and 30 percent of the width of the interior chamber. The retainer has an axial length. The axial length is between 85 and 90 percent of the height of the interior chamber.

A catheter is positionable through the cover. The catheter is removably received within the retainer. The catheter has a generally conical configuration. The catheter has an arcuate axis. The catheter has an axial length. The axial length of the catheter is greater than the height of the interior container. The axial length of the catheter is between 75 and 80 percent of the height of the retainer.

A plurality of similarly configured UVC panels are provided. The panels have lower ends. The lower ends of the panels are coupled to the floor of the exterior chamber between the exterior and interior chambers. The panels have upper ends. The upper ends of the panels are provided at an elevation adjacent to the open top of the exterior chamber. The panels are adapted to generate a minimum of 254 nanometers, which is considered to be optimal germicidal UVC wave length to irradiate the pathogens. In this manner it will eliminate most bacteria, fungus and spores on the catheter within the retainer.

A plurality of operational components is provided. The operational components are provided within and exterior of the operational chamber.

The operational components include a rechargeable battery. In this manner the system is operationally powered.

The operational components include a power cord. In this manner the battery is recharged the system is optionally powered.

The operational components include an operator controlled start switch. In this manner the operation of the system is initiated.

The operational components include a safety switch. The safety switch is provided on the floor of the exterior chamber. The safety switch is adapted to be activated upon positioning the interior chamber into the exterior chamber. In this manner operation of the system is precluded when the interior chamber is not within the exterior chamber.

The operational components include an adjustable timer. In this manner the panels are illuminated for a period of time up to 30 seconds that are needed to irradiate the pathogens, following depressing the start switch with the safety switch activated.

The operational components include an indicator light. The indicator light is provided in the exterior container between the base and the primary floor. In this manner a care giver is warned that the UVC panels are illuminated.

Further provided is a printed circuit board. The printed circuit board has operational components. In this manner the system may function.

Provided last is a door. The door has a hinge and a handle. In this manner access to the operational chamber is allowed for repair and reconstruction purposes.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims attached.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved anti-microbial catheter system which has all of the advantages of the prior art catheter systems of known designs and configurations and none of the disadvantages.

It is another object of the present invention to provide a new and improved anti-microbial catheter system which may be easily and efficiently manufactured and marketed.

It is further object of the present invention to provide a new and improved anti-microbial catheter system which is of durable and reliable constructions.

An even further object of the present invention is to provide a new and improved anti-microbial catheter system which is susceptible of a low cost of manufacture with regard to both materials and labor, and which accordingly is then susceptible of low prices of sale to the consuming public, thereby making such anti-microbial catheter system economically available to the buying public.

Even still another object of the present invention is to provide an anti-microbial catheter system for receiving and supporting and sanitizing a catheter, the receiving and supporting and sanitizing being done in a safe, sanitary, convenient and economical manner.

Lastly, it is an object of the present invention to provide a new and improved anti-microbial catheter system. An exterior container has a primary base, side walls and an open top. A primary floor is located in the exterior chamber and forms an operational chamber. An interior container has a square secondary floor, side walls and top. The interior container is removably received within the exterior container. A retainer is positioned within the interior chamber for receiving a catheter. A source of light is provided within the exterior chamber to irradiate the catheter.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a perspective illustration of an exterior container of anti-microbial catheter system constructed in accordance with the principles of the present invention.

FIG. 2 is a perspective illustration of an interior container of anti-microbial catheter system constructed in accordance with the principles of the present invention.

FIGS. 3 and 4 are plan views of the exterior and interior containers illustrated in FIGS. 1 and 2 taken along lines 3-3 and 4-4 of FIGS. 1 and 2.

FIG. 5 is a front elevational view of the anti-microbial catheter system shown in the prior Figures assembled for use.

The same reference numerals refer to the same parts throughout the various Figures.

DESCRIPTION OF THE PREFERRED EMBODIMENT

With reference now to the drawings, and in particular to FIG. 1 thereof, the preferred embodiment of the new and improved anti-microbial catheter system embodying the principles and concepts of the present invention and generally designated by the reference numeral 10 will be described.

The present invention, the anti-microbial catheter system 10 is comprised of a plurality of components. Such components in their broadest context include an exterior container, an interior container, a retainer and a source of light. Such components are individually configured and correlated with respect to each other so as to attain the desired objective.

First provided is an exterior container 14. The exterior container is in a rectilinear configuration. The exterior container has a square primary base 16. The exterior container has four similarly configured rectangular primary side walls 18. The exterior container has an open primary top 20. The exterior container has vertical primary supports 22. In this manner the primary side walls are secured together along abutting edges of adjacent primary side walls. The primary base and side walls form a rectilinear exterior chamber 24. The exterior container has a square primary floor 26. The primary floor is located in the exterior chamber in proximity to and above the base. An operational chamber 28 is provided. The operational chamber is located between the base and the primary floor. The exterior chamber has a height and a width. The primary side walls is fabricated of an opaque material.

An interior container 32 is provided. The interior container is in a rectilinear configuration. The interior container has a square secondary floor 34. The interior container has four similarly configured rectangular secondary side walls 36. The interior container has a secondary top 38. The interior container has vertical secondary spacers 40 along abutting edges of adjacent secondary side walls. The secondary base and side walls form a rectilinear interior chamber 42. The interior chamber has a height and a width. The interior container is removably received within the exterior container. The secondary side walls are fabricated of a transparent material.

A cover 46 is provided. The cover is fixedly positioned in the interior container. The cover has rigid segments 48. The cover has an elastomeric center 50. The center has slits 52. The slits are provided in a cross-shaped or star-shaped or X-shaped pattern. The segments have an exterior periphery. The periphery is attached to the interior secondary side walls.

A cylindrical retainer 56 is provided. The cylindrical retainer has an upper edge. The upper edge is located adjacent to the cover. The cylindrical retainer has a lower edge. The lower edge is attached to the secondary floor. The retainer has a diameter. The diameter of the retainer is between 25 and 30 percent of the width of the interior chamber. The retainer has an axial length. The axial length is between 85 and 90 percent of the height of the interior chamber.

A catheter 60 is inserted, and is positionable through the cover. The catheter is removably received within the retainer. The retainer will accommodate a catheter with a generally conical configuration. The catheter has an arcuate axis. The catheter has an axial length. The axial length of the catheter is greater than the height of the interior container. The catheter has an axial length. The axial length of the catheter is between 75 and 80 percent of the height of the retainer.

A plurality of similarly configured UVC panels 64 are provided, four in the primary embodiment. The panels have lower ends. The lower ends of the panels are coupled to the floor of the exterior chamber between the exterior and interior chambers. The panels have upper ends. The upper ends of the panels are provided at an elevation adjacent to the open top of the exterior chamber. The panels are adapted to generate a minimum of 254 nanometers, which is considered to be optimal germicidal UVC wavelength to irradiate the pathogens. In this manner it will eliminate most bacteria, fungus and spores on the catheter within the retainer.

A plurality of operational components is provided. The operational components are provided within and exterior of the operational chamber.

The operational components include a rechargeable battery 68. In this manner the system is operationally powered.

The operational components include a power cord 72. In this manner the battery is recharged the system is optionally powered.

The operational components include an operator controlled start switch 76. In this manner the operation of the system is initiated.

The operational components include a safety switch 80. The safety switch is provided on the floor of the exterior chamber. The safety switch is adapted to be activated upon positioning the interior chamber into the exterior chamber. In this manner operation of the system is precluded when the interior chamber is not within the exterior chamber.

The operational components include an adjustable timer 82. In this manner the panels are illuminated for a period of time up to 30 seconds that are needed to irradiate the pathogens, following depressing the start switch with the safety switch activated.

The operational components include an indicator light 86. The indicator light is provided in the exterior container between the base and the primary floor. In this manner a care giver is warned that the UVC panels are illuminated.

Further provided is a printed circuit board 90. The printed circuit board has operational components. In this manner the system may function.

Provided last is a door 96. The door has a hinge and handle. In this manner access to the operational chamber is allowed for repair and reconstruction purposes.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. An anti-microbial catheter system comprising:

an exterior container with a primary base and side walls and an open top, a primary floor located in the exterior chamber and forming an operational chamber;

an interior container with a square secondary floor and side walls and top, the interior container being removably received within the exterior container;

a retainer positioned within the interior chamber for receiving a catheter; and a source of light within the exterior chamber to irradiate the catheter.

2. The system as set forth in claim 1 and further including:

a plurality of operational components within and exterior of the operational chamber, the operational components including;

a source of electrical potential;

an operator controlled start switch for initiating the operation of the system;

a safety switch adapted to be activated upon positioning the interior chamber into the exterior chamber; and a timer to maintain the source of light illuminated following depressing the start switch with the safety switch activated.

3. The system as set forth in claim 1 wherein the source of light is a plurality of UVC panel.

4. An anti-microbial catheter system (10) for receiving and supporting and sanitizing a catheter, the receiving and supporting and sanitizing being done in a safe, sanitary, convenient and economical manner, the system comprising, in combination:

an exterior container (14) formed in a rectilinear configuration with a square primary base (16) and four similarly configured rectangular primary side walls (18) and an open primary top (20), vertical primary supports (22) securing the primary side walls together along abutting edges of adjacent primary side walls, the primary base and side walls forming a rectilinear exterior chamber (24), a square primary floor (26) located in the exterior chamber in proximity to and above the base and forming an operational chamber (28) between the base and the primary floor, the exterior chamber having a height and a width, the primary side walls being fabricated of an opaque material;

an interior container (32) formed in a rectilinear configuration with a square secondary floor (34) and four similarly configured rectangular secondary side walls (36) and a secondary top (38), vertical secondary spacers (40) along abutting edges of adjacent secondary side walls, the secondary base and side walls forming a rectilinear interior chamber (42), the interior chamber having a height and a width, the interior container being removably received within the exterior container, the secondary side walls being fabricated of a transparent material;

a cover (46) fixedly positioned in the interior container, the cover being formed of rigid segments (48) with an elastomeric center (50), the center having slits (52) in a cross-shaped pattern, the segments having an exterior periphery attached to the interior secondary side walls;

a cylindrical retainer (56) having an upper edge located adjacent to the cover, the cylindrical retainer having a lower edge attached to the secondary floor, the retainer having a diameter between 25 and 30 percent of the width of the interior chamber, the retainer having an axial length between 85 and 90 percent of the height of the interior chamber;

a catheter (60) positionable through the cover and removably received within the retainer, the catheter having a generally conical configuration with an arcuate axis, the catheter having an axial length greater than the height of the interior container, the catheter having an axial length between 75 and 80 percent of the height of the retainer;

a plurality of similarly configured UVC panels (64), the panels having lower ends coupled to the floor of the exterior chamber between the exterior and interior chambers, the panels having upper ends at an elevation adjacent to the open top of the exterior chamber, the panels adapted to generate a minimum of 254 nanometers, which is considered to be optimal germicidal UVC wavelength to irradiate and destroy most bacteria, fungus and spores on the catheter within the retainer;

a plurality of operational components within and exterior of the operational chamber, the operational components including;

a rechargeable battery (68) for optionally powering the system;

a power cord (72) for recharging the battery and optionally powering th system;

an operator controlled start switch (76) for initiating the operation of the system;

a safety switch (80) on the floor of the exterior chamber adapted to be activated upon positioning the interior chamber into the exterior chamber whereby operation of the system is precluded when the interior chamber is not within the exterior chamber;

an adjustable timer (82) to maintain the panels illuminated for a period of time up to 30 seconds following depressing the start switch with the safety switch activated;

an indicator light (86) on the exterior container between the base and the primary floor to warn a care giver that the UVC panels are illuminated;

a printed circuit board (90) with operational components for the functioning of the system; and a door (96) with a hinges and a handle to allow access to the operational chamber for repair and reconstruction purposes.

* * * * *